(12) United States Patent
Carlucci et al.

(10) Patent No.: US 6,191,340 B1
(45) Date of Patent: Feb. 20, 2001

(54) DISPOSABLE ABSORBENT ARTICLE HAVING A DECOUPLED, RANDOMLY ARRANGED ABSORBENT STRUCTURE

(75) Inventors: Giovanni Carlucci, Chieti; Nicola D'Alessio, Pescara; Gennaro Giorgini, Roseto; Maurizio Tamburro, Pescara, all of (IT)

(73) Assignee: The Procter & Gamble Company, Cincinnati, OH (US)

( * ) Notice: Under 35 U.S.C. 154(b), the term of this patent shall be extended for 0 days.

(21) Appl. No.: 09/202,961

(22) PCT Filed: Jun. 2, 1997

(86) PCT No.: PCT/US97/09284

§ 371 Date: Dec. 23, 1998

§ 102(e) Date: Dec. 23, 1998

(87) PCT Pub. No.: WO98/00084

PCT Pub. Date: Jan. 8, 1998

(30) Foreign Application Priority Data

Jul. 1, 1996 (EP) .................................................. 96110572

(51) Int. Cl.⁷ ....................................................... A61F 13/15
(52) U.S. Cl. ......................... 604/369; 604/375; 604/379; 604/385.04; 604/387
(58) Field of Search ..................................... 601/368–369, 601/375, 378–380, 383–384, 387, 385.1, 385.3, 385.4, 385.12

(56) References Cited

U.S. PATENT DOCUMENTS

| 3,512,530 | 5/1970 | Jones, Sr. . | |
| 3,954,493 | 5/1976 | Battista et al. . | |
| 4,475,911 | * 10/1984 | Gellert | 604/375 |
| 4,790,839 | * 12/1988 | Ahr | 604/378 |
| 5,021,050 | * 6/1991 | Iskra | 604/368 |
| 5,151,091 | * 9/1992 | Glaug et al. | 604/378 |
| 5,175,040 | * 12/1992 | Nguyen . | |
| 5,451,219 | * 9/1995 | Suzuki et al. | 604/369 |
| 5,624,423 | * 4/1997 | Anjur et al. | 604/369 |
| 5,895,379 | * 7/1975 | Litchholt et al. | 604/368 |
| 5,957,906 | * 9/1999 | Roe et al. | 607/378 |

FOREIGN PATENT DOCUMENTS

| 293208 | 7/1991 | (EP) . | |
| 2203827 | 5/1974 | (FR) . | |
| 1434643 | 5/1976 | (GB) . | |
| 91/09582 | * 7/1991 | (WO) | 604/378 |
| 95/00091 | 1/1995 | (WO) . | |
| 96/05790 | 2/1996 | (WO) . | |

* cited by examiner

Primary Examiner—John G. Weiss
Assistant Examiner—K. M. Reichle
(74) Attorney, Agent, or Firm—Ingrid N. Hickman; Jeffrey V. Bamber

(57) ABSTRACT

A disposable absorbent article which is substantially flat prior to use for wearing adjacent a body discharge area, having a body facing surface and a garment facing surface. The disposable absorbent article includes a liquid pervious topsheet, a backsheet, and an absorbent core intermediate the topsheet and backsheet. The absorbent core has a body facing surface and a garment facing surface, and has an expanding layer for expanding the article into a tridimensional structure while being worn by a user. The expanding layer includes a number of smaller expanding elements that are activated by body fluids, are decoupled from one another, and are capable of expanding substantially in only one direction upon activation by body fluids.

9 Claims, 2 Drawing Sheets

DISPOSABLE ABSORBENT ARTICLE HAVING A DECOUPLED, RANDOMLY ARRANGED ABSORBENT STRUCTURE

FIELD OF THE INVENTION

The present invention relates to disposable absorbent articles. Disposable absorbent articles are considered to be absorbent devices designed to be worn externally of the body by a user and to receive fluids discharged from the body. In particular the present invention relates to substantially flat disposable absorbent sanitary napkins, catamenials, incontinence inserts, pantiliners and diapers comprising an expanding layer. The expanding layer comprises a number of smaller expanding elements that are activated by body fluids and that are decoupled from one another, each smaller expanding element being capable of expanding substantially in only one direction.

BACKGROUND OF THE INVENTION

In their basic form, disposable absorbent articles comprise an absorbent core interposed between a pervious body-contacting element (alternatively referred to as a topsheet or an overwrap) and an impervious protective barrier (alternatively referred to as a backsheet). The absorbent element is, of course, intended to receive and contain the fluids discharged from the body. The body-contacting element is intended to provide comfortable and dry-feeling contact with body surfaces while allowing free passage of fluids therethrough into the absorbent element. The protective barrier is intended to prevent the fluids which are expelled or which escape from the absorbent element from soiling the user's garments.

In addition to the three functional elements mentioned above, disposable absorbent articles are generally provided with means for supporting the device adjacent the user's crotch area, where it can most effectively perform its intended function. Typically, absorbent articles as sanitary napkins are provided with an adhesive attachment means for securing the device to the inner crotch area of the user's undergarments.

Improved fluid interception can occur if the absorbent article is in close contact with the body of the wearer.

While previously known absorbent articles do perform their intended function, each conventional design can be further improved in one or more of absorbency of body fluids, protection of the user's garments from soiling, and/or physical comfort to the user.

With respect to disposable sanitary napkins several attempts have been made in the art to improve body contact with the wearer, and hence absorb fluids upon discharge and thereby minimize soiling, by providing a sanitary napkin having an anatomically shaped configuration, particularly including those that are raised upwardly or humped in their medial portions so as to be near or in contact with the pudendal region when worn.

On female users these sanitary napkins attempt to contact and absorb menses immediately as it leaves the vestibule.

Some articles have also been described in which an anatomically shaped configuration is provided during the wearing time, with the advantage of a better fit to the anatomy.

According to U.S. Pat. No. 3,512,530 a sanitary napkin is described in which a compressed regenerated cellulose sponge layer is combined to a larger fibrous cellulose layer to form a multiple ply absorbent core. The compressed regenerated cellulose sponge layer is positioned over the fibrous layer, and it is typically centered about it; it is intended as the primary absorbent element of the sanitary napkin, while the fibrous layer acts as a secondary or back up absorber.

The sanitary napkin may be therefore very thin prior to use, as compared to other sanitary products having the same absorbent capacity.

Although the compressed regenerated cellulose sponge layer is capable of expanding in Z-direction upon fluid absorption, the structure described is not particularly suitable to provide an effective body contact and might cause discomfort to the user.

When the expansion of the compressed regenerated cellulose sponge layer starts from the point that is first reached by the fluid, it is restrained by the surrounding, still dry regions of the sponge layer at least until they have received liquid by capillary diffusion through the material itself. This may not allow an effective swelling, particularly under absorption of relatively small amounts of fluid, due to the restraining effect of the remaining portions of the material not yet reached by the fluid.

The compressed regenerated cellulose layer may also be rather stiff in its dry state if a higher density, which is particularly useful for a rapid absorption and diffusion of the fluid, is to be provided to overcome this problem.

In European application EP96106724.6, filed on Apr. 29, 1996, an absorbent article is described which comprises a layer for expanding the article into a tridimensional structure while being worn by a user; the expanding layer is activated by body fluids and comprises incisions on at least its body facing surface or its garment facing surface that are arranged in a closed array of intersecting lines.

The incisions provide the expanding layer with the capability of achieving a high degree of swelling even in localized areas and upon activation by small amounts of fluid, and increase the layer flexibility.

Known hydrogel forming materials have been widely used to achieve absorbent layers activated by body fluids; such materials are capable of swelling and could also be used, in principle, to make an expanding absorbent layer. Hydrogel forming absorbent materials, commonly known as superabsorbents, are polymeric materials that can swell and absorb large quantities of liquid, particularly water and water containing fluids, such as body fluids; their use in absorbent articles is well known in the art.

The high absorption capacity of superabsorbents is not, however, combined with rapid absorption and this may adversely affect the performance of absorbent articles incorporating these substances. In fact, superabsorbents may give rise to a phenomenon defined in the prior art as "gel blocking"; when a particle of superabsorbent is in contact with the liquid, its external surface starts to absorb the liquid and swells obstructing the transmission of the liquid into the particle itself; the liquid can penetrate further into the still dry core of the particle only by means of a very slow diffusion mechanism.

Therefore it is desirable to provide an absorbent article with an anatomically shaped configuration for a closer body contact which is achieved during the use upon activation by absorbed body fluids, while it is comfortable for the wearer, easy to produce and to package, and capable of achieving a high degree of swelling even in localized areas and upon activation by small amounts of fluid, combined with the capability of a rapid acquisition and transmission of body fluids, particularly when viscous fluids like menses are to be managed, with an increased flexibility, and with an even better capability of conforming to the user's anatomy.

Hence, it is an object of the present invention to provide an expanding absorbent material that can make full use of its absorbent and expanding capacity without the limitations of the known hydrogel forming materials.

SUMMARY OF THE INVENTION

The present invention relates to disposable absorbent articles for wearing adjacent a body discharge area which are substantially flat prior to use. The substantially flat disposable absorbent article has a longitudinal centreline and a lateral centreline orthogonal thereto that define longitudinal and lateral directions respectively and a Z-direction which is orthogonal to both of them. The disposable absorbent article comprises a liquid pervious topsheet, a backsheet joined to said topsheet, and an absorbent core intermediate the topsheet and the backsheet. The term "substantially flat", as used herein, refers to articles which have their main extension in one plane in contrast to being shaped. The absorbent core comprises an expanding layer comprising a number of smaller elements that are activated by body fluids and that are decoupled from one another, each of the smaller elements being capable of expanding substantially in only one direction and at least two different smaller expanding elements being capable of expanding substantially in two non-parallel directions, respectively, and wherein the smaller expanding elements of the expanding layer are made of compressed regenerated cellulose sponge having a dry density of 0.1 to 1 g/cc.

BRIEF DESCRIPTION OF THE DRAWINGS

While the specification concludes with claims particularly pointing out and distinctly claiming the present invention, it is believed that the present invention will be better understood from the following description in conjunction with the following drawings:

DETAILED DESCRIPTION OF THE INVENTION

This invention relates to a disposable absorbent article which exhibits absorbency for bodily fluids, the protection of the user's garments from soiling, improved physical comfort to the user, and which is easy to produce and to package. The disposable absorbent article is described below by reference to a sanitary napkin or catamenial. The term "sanitary napkin", as used herein, refers to an article which is worn by females adjacent to the pudendal region and which is intended to absorb and contain the various body fluids which are discharged from the body (e.g., vaginal discharges, menses, and/or urine) and which is intended to be discarded after a single use. The disposable absorbent article is substantially flat prior to use.

The term "substantially flat", as used herein, refers to articles that have their main extension in one plane in contrast to being shaped. In a preferred embodiment a substantially flat article will have an absorbent core of constant thickness or, at least, will have an absorbent core that is not shaped in a direction which is orthogonal to the absorbent core itself. This does not exclude a general curvature of the absorbent core. It will be apparent to the man skilled in the art to which extent products can deviate from absolute flat shape and still benefit from the during the use shaping according to the present invention.

Sanitary napkins with longitudinal side cuffs, which may be optionally elasticated, and sanitary napkins with a moderate curvature are therefore within the scope of the present invention, provided that their absorbent core is not shaped prior to use in a direction that is orthogonal to the absorbent core itself.

The term "use", as used herein, refers to the period of time that starts when the absorbent article is actually put in contact with the anatomy of the user.

The terms "joined" or "affixed", as used herein, encompasses configurations whereby a first member is directly connected to a second member and configurations whereby a first member is indirectly connected to a second member by connecting the first member to intermediate members which in turn are connected to the second member.

The term "decoupled", as used herein, refers to the smaller expanding elements comprised in the expanding layer, which are distinct from one another though they can be in contact.

Interlabial devices which reside partially within and partially external of the wearer's vestibule are also within the scope of this invention. As used herein, the term "pudendal" refers to the externally visible female genitalia and is limited to the labia majora, the labia minora, the clitoris, and the vestibule.

Figure 1:
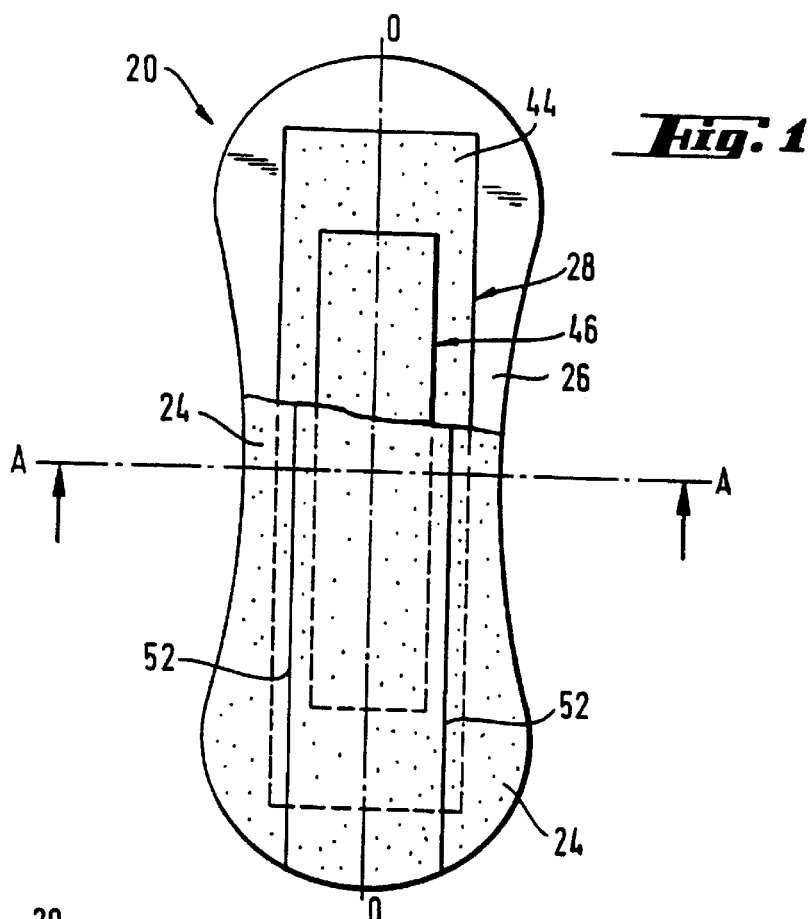
FIG. 1 is a partially cut away top plan view of one embodiment of a sanitary napkin according to the present invention.
Figure 2:
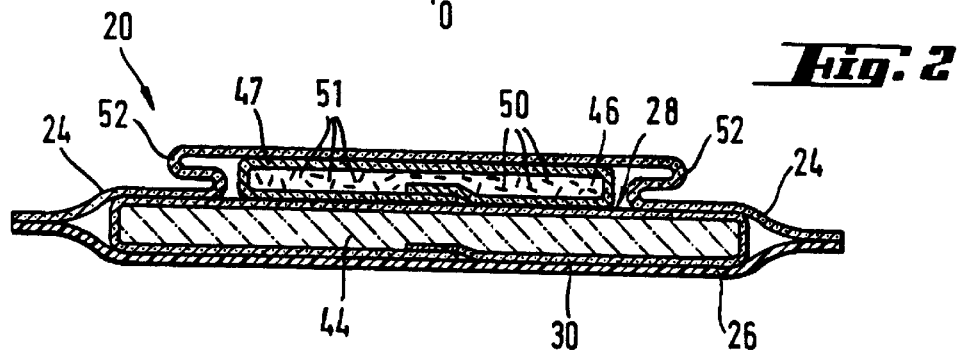
FIG. 2 is a cross-sectional view of the sanitary napkin shown in FIG. 1 as taken along a section line corresponding to the transverse centreline A—A.

In FIGS. 1 and 2, one preferred embodiment of a sanitary napkin 20 of the present invention is shown. FIG. 1 is a plan view of the sanitary napkin 20 of the present invention in its flat-out state prior to use with portions of the structure being cut-away to more clearly show the construction of the sanitary napkin 20 and with the portion of the sanitary napkin 20 which faces or contacts the wearer oriented towards the viewer. As shown in FIGS. 1 and 2, the sanitary napkin 20 preferably comprises a liquid pervious topsheet 24, a liquid impervious backsheet 26 joined to the topsheet 24, and an absorbent core 28 intermediate the topsheet 24 and the backsheet 26; the absorbent core 28 comprises an expanding layer 46 which is preferably capable of expanding the sanitary napkin into a tridimensional structure while being worn by a user.

Figure 3:
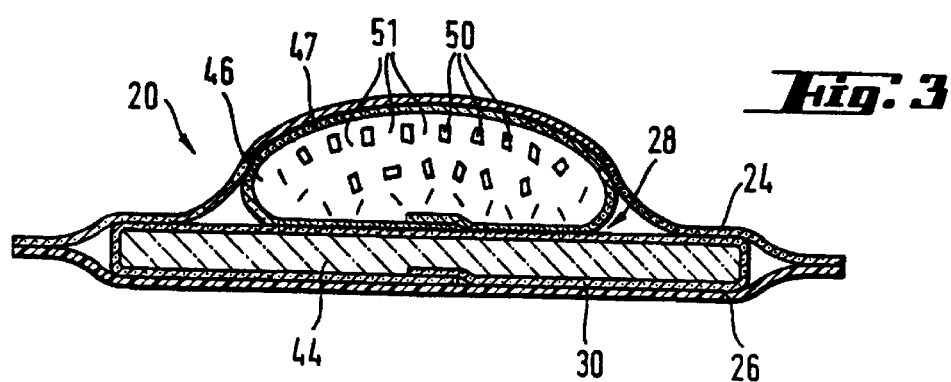
FIG. 3 is a cross-sectional view showing the sanitary napkin of FIG. 2 expanded into a tridimensional structure after activation during wear.

In a preferred embodiment of the present invention illustrated in FIGS. 1 to 3, the absorbent core 28 comprises the expanding layer 46 and a separate, substantially non expanding absorbent element 44 joined together and in face to face relationship to each other, the expanding layer 46 being positioned between the topsheet 24 and the absorbent element 44.

The absorbent element 44 and the expanding layer 46 may be associated in any suitable manner to form the absorbent core 28. Suitable manners include, but are not limited to, associating the absorbent element 44 and the expanding layer 46 with adhesives such as by spray-gluing or by applying lines or spots of adhesive between them. Alternatively, or additionally, the association between the layers may be achieved by fibre entanglement or by a plurality of discrete fusion bonds.

Alternatively, the expanding layer 46 may constitute the entire absorbent core 28.

The absorbent capacity of the absorbent core 28 should be compatible with the intended body fluid loading for the sanitary napkin 20. Further, the overall absorbent capacity of the absorbent core 28 may be varied to accommodate wearers ranging in the expected amount of body fluid volume. For instance, a different absorbent capacity may be utilized for sanitary napkins intended for day time use as compared with those intended for night time use, or for sanitary napkins intended for use by teenage females as compared with those intended by more mature women.

The sanitary napkin 20 has two surfaces, a body contacting or facing surface, and a garment facing or contacting surface. The absorbent core 28 has corresponding body facing and garment facing surfaces. The sanitary napkin 20 has two centrelines, a longitudinal centreline O—O and a transverse centreline A—A orthogonal thereto. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral", as used herein, are interchangeable, and refer to a line, axis, or direction which lies within the plane of the sanitary napkin 20 and is generally perpendicular to the longitudinal direction. The Z-direction is orthogonal to both the longitudinal and lateral directions of the sanitary napkin 20 and extends outwardly from the plane of the sanitary napkin 20, which is defined by the longitudinal centreline O—O and the lateral centreline A—A. The term "longitudinally oriented" refers to a direction ±45 degrees of the longitudinal direction in the plane of the sanitary napkin 20; the term "laterally oriented" refers similarly to any other direction in the plane of the sanitary napkin 20.

The long edges of the sanitary napkin 20, which are aligned with the longitudinal centreline O—O, are the longitudinal side margins of the sanitary napkin 20. The ends of the sanitary napkin 20 joining the longitudinal side margins are the transverse ends of the sanitary napkin 20. Collectively the longitudinal side margins and transverse ends of the sanitary napkin 20 define its periphery. Similarly, the absorbent core 28 of the sanitary napkin 20 have a periphery defined by alternatively disposed longitudinal side margins and transverse ends.

Tridimensional structures of the sanitary napkin 20 are those preferred structures in which the sanitary napkin structure is caused to expand, at least partially, in the Z-direction, in order to more closely conform to the user's anatomy. Said expansion preferably takes place in a direction that goes from the garment facing surface towards the body facing surface of the sanitary napkin 20. Particularly preferred are tridimensional structures with a convex upward configuration that are inclusive of, but not limited to, inverted U-shapes or inverted V-shapes, with "convex upward configuration" being meant a structure of the sanitary napkin that is convex on its body facing surface. With these preferred configurations the cross-sectional contour of the central portion of the sanitary napkin more closely matches the labia of the typical wearer.

The topsheet 24 is compliant, soft feeling, and non-irritating to the wearer's skin. Further, the topsheet 24 is liquid pervious, permitting liquid to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibres (e.g., wood or cotton fibers), synthetic fibres (e.g., polymeric fibres such as polyester, polypropylene, or polyethylene fibres); or from a combination of natural and synthetic fibres.

A preferred topsheet comprises an apertured formed film. Apertured formed films are preferred for the topsheet because they are pervious to body fluids and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer.

Suitable formed films are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991. A preferred topsheet for the absorbent article of the present invention is a formed film described in one or more of the above patents and marketed on sanitary napkins by The Procter & Gamble Company of Cincinnati, Ohio as DRI-WEAVE® apertured film topsheet.

In a preferred embodiment of the present invention, the body or exposed surface of the formed film topsheet is hydrophilic so as to help liquid transfer through the topsheet faster than if the body surface were not hydrophilic so as to diminish the likelihood that menstrual fluid will flow off the topsheet rather than flowing into and being absorbed by the absorbent core.

The topsheet of the present invention is preferably capable of expanding as the sanitary napkin 20 expands in a tridimensional structure upon absorption of body fluids. This may be achieved when the topsheet is made of a material that is intrinsically extensible under the forces exerted by the expanding layer 46. In a preferred embodiment illustrated in FIGS. 1 and 2 the topsheet 24 is provided with two pleats or folds 52 symmetrically positioned at both sides of the longitudinal centreline O—O and substantially parallel to it. As shown in FIG. 2 the topsheet 24 in each pleat or fold 52 is folded twice on itself toward the longitudinal side margins of the sanitary napkin 20. A single pleat or fold or, alternatively, more than two folds may be also comprised in the topsheet 24 without departing from the scope of the present invention; the pleats or folds may be generally longitudinally or laterally oriented.

The backsheet 26 is impervious to liquids (e.g., menses and/or urine) and is preferably manufactured from a thin plastic film, although other flexible liquid impervious materials can also be used. In use, the backsheet 26 is interposed between the absorbent core 28 and the user's undergarments. The function of the backsheet 26 is to prevent exudates which may be expelled from or which inadvertently bypass the absorbent core 28 from contacting and soiling the user's undergarments. The backsheet 26 can thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm to about 0.015 mm. The backsheet 26 is preferably embossed and/or matte finished to provide a more clothlike appearance.

In a preferred embodiment of the present invention the sanitary napkin 20 is also provided with a panty fastening means, not shown in the figures for clarity, which provides means to attach the article to an undergarment. For example the panty fastening means may comprise a mechanical fastener such as hook and loop fasteners such as marketed under the tradename VELCRO, snaps or holders. Alternatively, the sanitary napkin 20 is fastened to the undergarment by means of panty fastening adhesive on the backsheet 26. The panty fastening adhesive provides a means for securing the sanitary napkin 20 to the panty and preferably a means for securing the sanitary napkin 20 when soiled to the fold and wrap package for convenient disposal. Typically, at least a portion of the garment facing surface of the backsheet 26 is coated with adhesive to form the panty fastening adhesive. Any adhesive or glue used in the art for such purposes can be used for the panty fastening adhesive herein. Pressure sensitive adhesives are most preferred. Suitable adhesives include Century A-305-IV manufactured by the Century Adhesives Corporation of Columbus, Ohio, and Instant LOK 34-2823 manufactured by the National Starch and Chemical Company of Bridgewater, N.J, 3 Sigma 3153 manufactured by 3 Sigma and Fuller H-2238ZP manufactured by the H.B. Fuller Co.

The panty fastening adhesive is typically applied to the backsheet by slot coating or spraying in various distribution patterns, such as e.g. continuous or discontinuous strips, intermittent dots, random spiral patterns.

The panty fastening adhesive is typically covered with a removable releas e paper or film in order to prevent the adhesive from drying out or adhering to another surface other than the panty prior to use. Any commercially available release paper or film may be used. Suitable examples include BL 30MG-A SILOX EI/O and BL 30 MG-A SILOX 4 P/O available from Akrosil Corporation.

If present, as illustrated in FIGS. 1 to 3, the substantially non expanding absorbent element 44 of the absorbent core 28 may be any absorbent means which is generally compressible, resilient, non-irritating to the wearer's skin and capable of absorbing and containing body fluids. The absorbent element 44 may be manufactured from a wide variety of liquid absorbent materials commonly used in disposable sanitary napkins, and other disposable absorbent articles. Examples of suitable absorbent materials include comminuted wood pulp (which is generally referred to as airfelt), creped cellulose wadding, modified cross-linked cellulose fibres (such as those described in U.S. Pat. No. 5,217,445 issued to Young, et al. on Jun. 8, 1993), capillary channel fibres (that is, fibres having intra-fibre capillary channels such as those described in U.S. Pat. No. 5,200,248 issued to Thompson, et al. on Apr. 6, 1993), absorbent foams (such as those described in U.S. Pat. No. 5,260,345, issued to DesMarais, et al. on Nov. 9, 1993 and U.S. Pat. No. 5,268,244 issued to DesMarais, et al. on Dec. 7, 1993), thermally bonded airlaid materials (such as those material described in U.S. patent application Ser. No. 08/141,156, entitled "Catamenial Absorbent Structures Having Thermally Bonded Layers For Improved Handling of Menstrual Fluids and Their Use In Catamenial Pads Having Improved Fit and Comfort" filed in the name of Richards, et al. on Oct. 21, 1993), absorbent sponges, synthetic staple fibres, polymeric fibres, hydrogel-forming polymer gelling agents, peat moss, or any equivalent materials or combinations of materials. Suitable absorbent cores comprising foams are described in European Applications 0 598 833, 0 598 823 and 0 598 834.

In the embodiment illustrated in FIGS. 1 to 3, the absorbent element 44 of the absorbent core 28 comprises an absorbent layer 30 made of a thermally bonded airlaid material longitudinally folded twice on itself and comprising particles of absorbent gelling material therebetween, which are not shown for clarity.

As shown in FIGS. 1 and 2 the absorbent core 28 comprises an expanding layer 46 that preferably is capable of expanding the sanitary napkin 20 into the desired tridimensional structure while the sanitary napkin 20 is being worn. In an embodiment illustrated in FIGS. 1 to 3 the expansion and the final shaping of the sanitary napkin 20 into the preferred tridimensional structure is provided by the swelling, substantially in Z-direction, of the expanding layer 46 that is activated during wear by the absorption of body fluids.

The expanding layer 46 comprises a number of smaller expanding elements 50 that are decoupled, that is, are distinct from one another; each of said smaller expanding elements 50 is capable of expanding substantially in only one direction upon activation of body fluids, that is, upon absorption of fluid, each single smaller expanding element 50 will not swell uniformly along the three dimensions of the space, but will rather increase substantially only one of its three dimensions.

The smaller expanding elements 50 are randomly distributed within the expanding layer 46, and different smaller expanding elements 50 expand in directions that are not parallel to one another.

The expanding layer 46 may comprise any material that is capable of such swelling, preferably in order to shape the sanitary napkin 20 into a desired tridimensional structure.

After the absorption of body fluids and the subsequent swelling, the material of the smaller expanding elements 50 comprised in the expanding layer 46 must be soft, compliant, conformable and resilient. It must be compressible such that it will deform under the relatively small forces that are experienced during normal use. In addition to be compressible, the material of the smaller expanding elements 50 of the expanding layer 46 must be flexible and conformable after swelling so it can preferably provide improved fit through the topsheet 24 into and around the wearer's labia and perineum when the tridimensional structure is formed during the wearing time. The ability to follow the topography of the anatomy will provide intimate contact with the exposed genitalia of the female user. This helps provide better fluid transfer from the user into the expanding layer 46. While these characteristics of the expanding layer 46 allow for improved fit, they also cause the product to be both soft and comfortable for the wearer.

It is preferred that the expanding layer 46 forms at least part of the body facing surface of the absorbent core 28. In the embodiment illustrated in FIGS. 1 and 2 the expanding layer 46 is positioned over the absorbent element 44, in face to face relationship with it; it is rectangular and preferably narrower and shorter than the absorbent element 44, as illustrated in FIG. 1, being centered about both the longitudinal and transverse centrelines O—O and A—A. As an alternative, different shapes are also possible for the expanding layer 46, e.g. an hourglass shape.

The expanding layer 46 of the absorbent core 28 has a body facing surface and a garment facing surface and comprises a number of smaller expanding elements 50 that are randomly distributed. As illustrated in FIGS. 1 and 2 the expanding layer 46 comprises a fluid permeable sheet 47, e.g. a preferably hydrophilic nonwoven or tissue layer, longitudinally folded twice on itself with overlapping longitudinal edges joined to each other by known means, e.g. by gluing; the folded nonwoven sheet 47 is also joined to itself at its transverse ends, e.g. by means of lines of glue. The smaller expanding elements 50 are randomly distributed within the folded nonwoven sheet 47.

Preferably the expanding layer 46 is made in such a way that it is not restrained from swelling upon activation by body fluids of the smaller expanding elements 50 comprised therein; this may be achieved in one of the ways known in the art; when, as it is illustrated in FIGS. 1 and 2, the smaller expanding elements 50 are encased in a fluid permeable sheet 47, said sheet 47 can be made e.g. of a material that is intrinsically extensible under the forces exerted by the expanding layer 46, or, alternatively, it can be somewhat larger than what is needed to encase the smaller expanding elements 50 in their dry, unexpanded condition, so allowing their complete expansion upon activation by body fluid without any restraining effect.

Smaller expanding elements 50 can be made in any regular or irregular shape; a preferred shape is the parallelepipedal shape with two square bases, but alternate shapes are also possible, e.g. smaller expanding elements 50 with cubic shape or cylindrical shape having circular or oval bases, as well as smaller elements 50 having the shape of a cone or of a pyramid, or of a truncated cone or truncated pyramid.

The smaller expanding elements 50 can also comprise slits or incisions or apertures in their surface, or combinations thereof.

The smaller expanding elements 50 that are comprised in the expanding layer 46 can all have the same shape, or, alternatively, different shapes.

Each smaller element 50 can have a volume comprised between 0.1 mm$^3$ and 150 mm$^3$, preferably from 4 mm$^3$ to 50 mm$^3$, more preferably from 10 mm$^3$ to 35 mm$^3$. The smaller expanding elements 50 comprised in the expanding layer 46 can all have the same volume, or, alternatively, smaller expanding elements 50 having different volumes can be comprised in different zones of the expanding layer 46, e.g., smaller expanding elements of smaller volume can be comprised in the portion of the expanding layer 46 which is intended to receive the fluid first; this can be the central portion of the expanding layer 46.

The smaller expanding elements 50 that are randomly distributed within the expanding element 46 can be in direct contact to one another, provided that they are decoupled, further comprising void spaces 51 among them; alternatively, they can comprise other materials among them, preferably another absorbent material, e.g., absorbent fibres.

Basis weights for the expanding layer 46 can range from 20 g/m$^2$ to 5000 g/m$^2$, preferably from 300 g/m$^2$ to 1300 g/m$^2$, the smaller expanding elements 50 constituting from 10% to 100% of the total dry weight of the expanding layer 46.

Smaller expanding elements 50 and, if present, other materials such as absorbent fibres are preferably uniformly distributed within the expanding layer 46, or, alternatively, the smaller expanding elements 50 can be distributed non uniformly within the expanding layer 46, e.g., smaller expanding elements 50 can be mostly distributed in the portion of the expanding layer 46 which is intended to receive fluid first, i.e. in its central portion.

The smaller expanding elements 50 are preferably not joined to one another or to any other element of the expanding layer 46, e.g., the nonwoven sheet 47 that encases them or the other material optionally comprised in the expanding layer 46; nevertheless, a certain degree of bonding of the smaller expanding elements 50 can be achieved, while they are still decoupled from one another, in order to maintain a stable distribution of the smaller expanding elements 50 within the expanding layer 46, provided that the smaller expanding elements 50 are substantially free of expanding upon activation by body fluids without being restrained by the surrounding material of the expanding layer 46 and by the bonding material that can be optionally used. This may be done with any method that is known to the man skilled in the art. When, as it is alternatively considered, absorbent fibres are distributed among the smaller expanding elements 50, they can provide the smaller expanding elements 50 with a stable distribution within the expanding layer 46 without any restraining effect when the swelling takes place.

Each smaller expanding element 50 comprised in the expanding layer 46 is substantially free of expanding upon activation by body fluid along its only one direction, being substantially independent from any other smaller expanding element 50, and different smaller expanding elements 50 typically expand in directions that are not parallel to one another. The expansion of each smaller element 50 is not restrained by the surrounding smaller expanding elements 50 possibly not yet reached by the fluid. This allows a much higher absorption capacity and swelling even in localized zones of the expanding layer 46 upon absorption of very limited amounts of fluid, as may happen when the first drops of body fluid are received by the expanding layer 46. The expanding layer 46 has moreover a very high flexibility, even in its dry state before the absorption of body fluids; therefore the sanitary napkin 20 is more comfortable for the wearer.

When, as it is preferred, the expanding layer 46 is capable of expanding the sanitary napkin 20 into a tridimensional structure while being worn by the user, upon activation by absorbed body fluids, the smaller expanding elements 50 comprised in the expanding layer 46 provide the expanding layer 46 with a better capability of conforming to the user's anatomy, owing to the fact that they are substantially independent from one another and therefore each smaller element 50 can swell freely along its own one direction.

FIGS. 2 and 3 show the sanitary napkin 20 before and after expansion of the expanding layer 46 respectively.

FIG. 2 shows the sanitary napkin 20 before the first fluid absorption, with the expanding layer 46 prior to swelling. FIG. 3 shows a preferred embodiment of the sanitary napkin 20 expanded into a tridimensional structure after activation of the expanding layer 46 upon absorption of a first amount of body fluid in its central zone. The first release of fluid is rapidly acquired within the void spaces 51 comprised among the smaller expanding elements 50 first reached by the fluid; the void spaces 51 provide the expanding layer 46 with a path for initial fluid acquisition among the smaller expanding elements 50, so allowing a quick and effective swelling. The void spaces 51 provide the expanding layer 46, even after its swelling, with a larger void volume available for the acquisition of further releases of fluid and with a direct path through the expanding layer 46 for the fluid transmission to the substantially non expanding absorbent element 44.

Upon absorption of this first amount of body fluid, the smaller expanding elements 50 of the expanding layer 46 that are first reached by the fluid are capable of swelling completely independently of the surrounding smaller expanding elements possibly not yet reached by the fluid, without being restrained by them. The zone of the expanding layer 46 that first receives the fluid may therefore swell more than if it were not formed by decoupled, smaller expanding elements 50 that are distinct from one another.

Each smaller expanding element 50 is capable of expanding along only one direction, and since they are randomly distributed within the expanding layer 46, they will expand in many different directions non parallel to one another if considered individually; the preferred overall effect of such separate different swellings will be a swelling of the expanding layer 46 substantially in the Z-direction, as illustrated in FIG. 3.

The absorption of the fluid within the expanding layer 46 is promoted by the void spaces 51 that increase the surface area available for the fluid acquisition and distribution and provide a preferential path for the diffusion of the fluid within the expanding layer 46 itself. This allows a higher acquisition speed of viscous body fluids as menses and vaginal discharges and provides an effective management of sudden gushes of fluid.

In case of release of particularly heavy fluid gushes the void spaces 51 create a straight path for sending directly into the substantially non expanding absorbent element 44 of the absorbent core 28, through the nonwoven of the substrate 54, at least that portion of the fluid that may not be completely acquired with in the expanding layer 46.

In a random distribution of the smaller expanding elements 50 into the expanding layer 46 the dimension of the void spaces 51 can be roughly linked to the volume of the smaller expanding elements 50, that is, the greater the volumes of the smaller expanding elements 50, the larger the dimension of the void spaces 51 comprised among them.

The volume of the smaller elements 50 and the dimensions of the void spaces 51 can be constant throughout the entire extension of the expanding layer 46, or, alternatively, different dimensions of the void spaces 51 and different volumes of the smaller elements 50 can be adopted in different portions of the expanding layer 46. Smaller volumes of the smaller elements 50 generally provide a higher and more uniform swelling upon activation by even very small amounts of fluid, while larger volumes of the void spaces 51 increase the capability of the expanding layer 46 of acquiring sudden gushes of fluid and of transmitting the excess fluid through the thickness of the expanding layer 46; smaller volumes of the void spaces 51, on the other hand, increase the capability of the expanding layer 46 of diffusing fluid far from the point that is first reached by the fluid.

The right balance among all these different features can be easily defined by the man skilled in the art.

If absorbent fibres are comprised among the smaller expanding elements 50 of the expanding layer 46, they can improve the acquisition and the diffusion of the fluid among the smaller expanding elements 50.

In a preferred embodiment of the present invention the expanding layer 46 comprises smaller expanding elements 50 made form a sheet of compressed regenerated cellulose sponge.

The regenerated cellulose sponge that preferably constitutes the expanding layer 46 is a material that is known in the art; examples of suitable materials are described in U.S. Pat. No. 3,954,493, in French Patent Application FR-A-2,203, 827, and in European Patent EP-B-0 293 208. The regenerated cellulose sponge is a sponge of a material containing a cellulose skeleton. Examples of such sponges include, in addition to sponges consisting of cellulose itself, sponges consisting of a cellulose derivative as viscose, a cellulose ether and a cellulose ester, and sponges consisting of mixtures of those materials.

By way of example only, a regenerated cellulose sponge may be prepared from a mixture of a viscose solution with reinforcing fibres and a porogenic compound, e.g. crystals of sodium sulphate decahydrate or of another alkali metal salt with a high content of crystallized water, the final pore dimension being related to that of the salt crystals. The viscose solution may be extruded through an extrusion die of the desired section, then let coagulate. The material is washed with water after regeneration in order to eliminate the salt and other possible soluble compounds, then it is dried and, if necessary, compressed to the desired density.

The compressed regenerated cellulose sponge has a network structure that contains air bubbles created by the elimination of the sodium sulphate crystals.

The compressed regenerated cellulose sponge material is available in various forms, e.g. in layers or sheets of different densities, thicknesses and basis weights; dry densities values for the compressed material used for the expanding layer 46 of the present invention are from 0.1 g/cc to 1 g/cc, while thicknesses may range from 0.5 mm to 5 mm.

The swelling upon liquid absorption of the compressed regenerated cellulose sponge material that forms the expanding layer 46 takes place substantially in the direction of the compression and restores the pore size of the regenerated sponge before the compression; it creates a void volume that does not collapse in wet conditions and therefore enables the material to rapidly acquire further releases of fluid and to transmit them to the underlying absorbent element 44 of the absorbent core 28.

The smaller expanding elements 50 of the present invention can be achieved by cutting in the desired shape a sheet of compressed regenerated cellulose sponge of the appropriate thickness.

In the embodiment illustrated in FIGS. 1 to 3 the total absorbent capacity of the sanitary napkin 20 is provided for by an absorbent core 28 that comprises and expanding layer 46 comprising smaller elements 50 cut form a sheet of compressed regenerated cellulose sponge, and an absorbent element 44.

In a preferred embodiment of the present invention, which is illustrated in FIGS. 1 and 2, the absorbent core 28 comprises a substantially non expanding absorbent element 44 and an expanding layer 46 constituted by smaller elements 50 of compressed regenerated cellulose sponge with a dry volume of between 0.1 $mm^3$ and 150 $mm^3$, a dry density of 0.5 g/cc with a parallelepipedal shape having square bases with a 2 mm side and a thickness of 1 mm, randomly distributed in the expanding element 46 with a uniform basis weight of 1000 $g/m^2$. Each smaller element 50 is compressed in the direction of its thickness and therefore, upon activation by body fluid, it is capable of expanding substantially along this direction only.

The smaller expanding elements 50 are encased within a nonwoven sheet 47 made of a hydrophilic thermal bonded polypropylene nonwoven with a basis weight of 20 g/m² longitudinally folded twice on itself with overlapping longitudinal edges on the garment facing surface of the expanding layer 46 joined to each other by a line of adhesive; a line of adhesive joins the folded nonwoven sheet on itself at both its transverse ends, in order to define a closed space that can comprise the smaller expanding elements 50 within it. The expanding layer 46 is rectangular and comprises alternatively disposed longitudinal side margins and transverse ends being 125 mm long and 30 mm long, respectively. The expanding layer 46 is positioned on the body facing side of the absorbent element 44 in face to face relationship with it, both being centered about both longitudinal and transverse centrelines O—O and A—A of the sanitary napkin 20. The absorbent element 44 of the absorbent core 28 is 207 mm long and 64 mm wide. Suitable sheets of compressed regenerated cellulose sponge may be those produced by Spontex France.

The compressed regenerated cellulose sponge that preferably constitutes the expanding layer 46 is capable of absorbing body fluids quickly with a large increase in its volume, generally from about 2 to 20 times, and usually from 5 to 15 times its volume at the time of the compression. The volume increase substantially corresponds to a swelling in the direction of the compression.

The sanitary napkin 20 is produced and packaged as a conventional flat product, as illustrated in FIGS. 1 and 2. After the sanitary napkin 20 has been worn, as soon as the absorbed body fluids come in contact with the expanding layer 46, this will begin to swell increasing its thickness, as can be seen in FIG. 3. The topsheet 24 follows the swelling of the expanding layer 46 by straightening out the pleats or folds 52, therefore increasing its width without restraining the swelling.

The swelling of the compressed regenerated cellulose sponge that constitutes the smaller expanding elements 50 of the expanding layer 46 takes place only upon activation by the absorbed fluid, that is only during the use of the sanitary napkin 20 and in close contact with the user's anatomy; the preferred formation of the tridimensional structure can therefore achieve a much better fit with the anatomy of the user. Moreover, the swelling of the smaller expanding elements 50 of the expanding layer 46 can start where it is actually reached by the fluid first; the preferred formation of the tridimensional structure can also fit, therefore, the different possible ways in which the body fluids may be released by various users.

The smaller elements 50 randomly distributed that constitute the expanding layer 46 make it possible a higher and localized swelling of the smaller elements 50 that are actually reached by the body fluid, without the restraining effect of the surrounding, still dry portions of the expanding layer 46; this allows the expanding layer 46 to conform more effectively to the user's anatomy, even upon activation by very small amounts of body fluid.

The void spaces 51 allow a more effective management of sudden gushes of fluid and a better diffusion of fluid within the expanding layer 46, therefore promoting a higher and more rapid swelling even under absorption of small amounts of viscous body fluids.

The expanding topsheet 24, which is a preferred feature of the sanitary napkin 20, also provides a comfortable contact with the user's anatomy, without restraining the expansion of the sanitary napkin 20 into the desired tridimensional structure upon activation by body fluids.

The sanitary napkin 20 of the present invention is flat prior to use, and may be therefore manufactured and packaged more easily than a conventional elasticated or preformed article. Since the preferred tridimensional structure is formed only during the use, the sanitary napkin of the present invention is also easier to wear.

In an alternate embodiment of the present invention, the sanitary napkin 20 may have two flaps (not shown), each of which are adjacent to and extend laterally from the side edge of the absorbent core. The flaps are configured to drape over the edges of the wearer's panties in the crotch region so that the flaps are disposed between the edges of the wearer's panties and the wearer's thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment facing surface so that the flaps can be folded back under the panty and attached to the garment facing side of the panty. In this way, the flaps serve to keep the sanitary napkin properly positioned in the panty.

The flaps may be constructed of various materials including materials used for the topsheet 24, backsheet 26, combinations thereof, and may be a laminate having tissue in the centre. Further, the flaps may be a separate element attached to the main body of the sanitary napkin 20 or can comprise extensions of the topsheet 24 and/or backsheet 26. It is recommended, however, that the flaps have a liquid impervious backsheet to prevent body fluids which reach the flaps from soiling the edges of the wearer's panties.

Preferred flaps that are suitable or adaptable to the sanitary napkin 20 of the present invention are disclosed in U.S. Pat. No. 4,687,478 issued to Van Tilburg on Aug. 18, 1987; U.S. Pat. No. 4,589,876 issued to Van Tilburg on May 20, 1986; and U.S. Pat No. 4,608,047 issued to Mattingly on Aug. 26, 1986.

Optionally, the sanitary napkin 20 may comprise components that naturally wrap the sides of a wearer's panties. Sanitary napkins having components that naturally wrap the sides of a wearer's panties suitable for use with the sanitary napkin 20 of the present invention are disclosed in U.S. patent application Ser. No. 08/096,121 entitled "Absorbent Article having Panty Covering Components that Naturally Wrap the Sides of Panties", filed Jul. 22, 1993, in the names of Lavash, et al and U.S. patent application Ser. No. 08/277733 entitled "Absorbent Articles Having Undergarment Covering Components with Zones of Extensibility", filed Jul. 20, 1994, in the names of Weinberger, et al.

The expanding layer 46 for expanding the sanitary napkin 20 into a tridimensional structure during wear can be comprised in the sanitary napkin 20 in any other suitable position and/or orientation in order to get the desired tridimensional structure, in particular it can form at least part of the garment facing surface of the absorbent core 28.

The fluid permeable sheet 47 that, according to a preferred embodiment, encases the smaller expanding elements 50 to constitute the expanding layer 46, can also be constructed in such a way that it can direct the swelling of the smaller expanding elements 50, and therefore of the whole expanding layer 46, upon activation by absorbed body fluids, into a preferred shape.

An optional component that can be included in the sanitary napkin 20 of the present invention is an odour control means; any suitable odour control means can be incorporated in the sanitary napkin of the present invention in any desired form, according to the techniques well known in the art.

Figure 4:
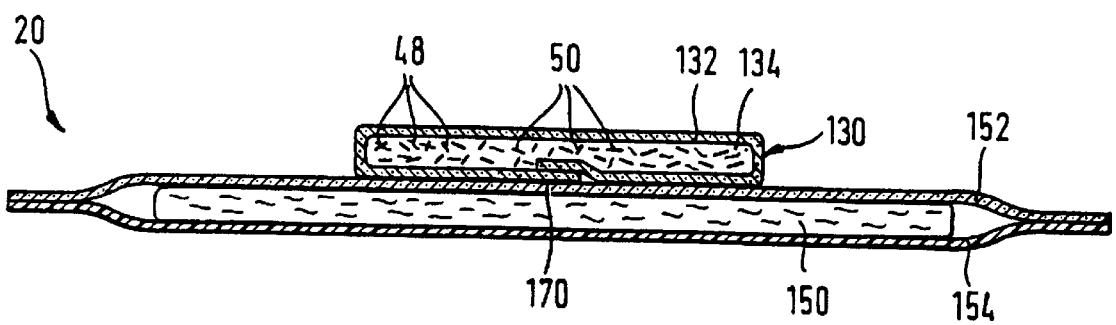
FIG. 4 is a cross-sectional view similar to that of FIG. 2 of another embodiment of a sanitary napkin according to the present invention.

In an alternative embodiment illustrated in FIG. 4 a compound sanitary napkin 20 similar to those disclosed in International application WO 96/05790 is described, which comprises a primary absorbent member 130 and a secondary absorbent member 150 which is larger than said primary absorbent member 130; the primary absorbent member 130 and the secondary absorbent member 150 have a common length and are joined together by union means 170 in such a manner that the longest unattached distance between adjacent points of attachment is less than 75% of said common length. The primary absorbent member 130 comprises an absorbent core 134 and a liquid permeable topsheet 132 that completely encases the absorbent core 134; the topsheet 132 of the primary absorbent member 130 is joined by the union means 170 to the topsheet 152 of the secondary absorbent member 150 and, in turn, to the backsheet 154 of the secondary absorbent member 150. The absorbent core 134 of the primary absorbent member 130 comprises smaller expanding elements 50 uniformly distributed with airfelt fibres 48 within the topsheet 132; in this embodiment the absorbent core 134 of the primary absorbent member 130 corresponds to the expanding layer 46.

Figure 5:
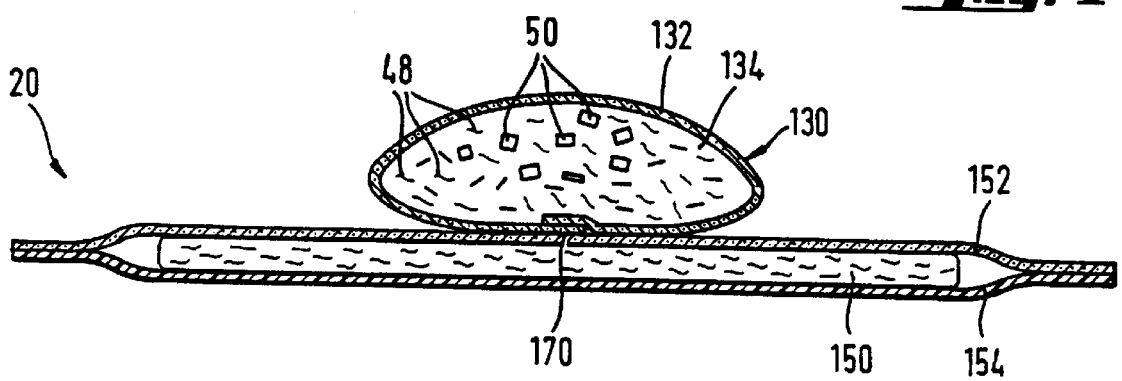
FIG. 5 is a cross-sectional view showing the sanitary napkin of FIG. 4 expanded in a tridimensional structure after activation during wear.

FIG. 5 shows the sanitary napkin of FIG. 4 after swelling upon activation by a first release of body fluid; the fluid has reached the smaller expanding elements 50 that are nearer to the point of acquisition, both directly, and by means of diffusion through the absorbent fibres comprised among the smaller expanding elements 50. The smaller elements 50 reached by the fluid have swelled, each one along only one direction, typically corresponding to the direction of compression when the smaller expanding elements 50 are made of compressed regenerated cellulose sponge. The overall effect of the expansion of the randomly distributed smaller elements 50 consists in the swelling, substantially in Z-direction, of the primary absorbent member 130. The topsheet 132 that encases the absorbent core 134 shall be preferably made in such a manner that it does not restrain the expansion of the expanding layer 46, as it is known in the art; it can be made e.g. of a material that is intrinsically extensible under the forces exerted by the expanding layer 46, or, alternatively, it can be somewhat larger than what is needed to encase the absorbent core 134 in its dry, unexpanded condition, so allowing its complete expansion upon activation by body fluid without any restraining effect.

Figure 6:
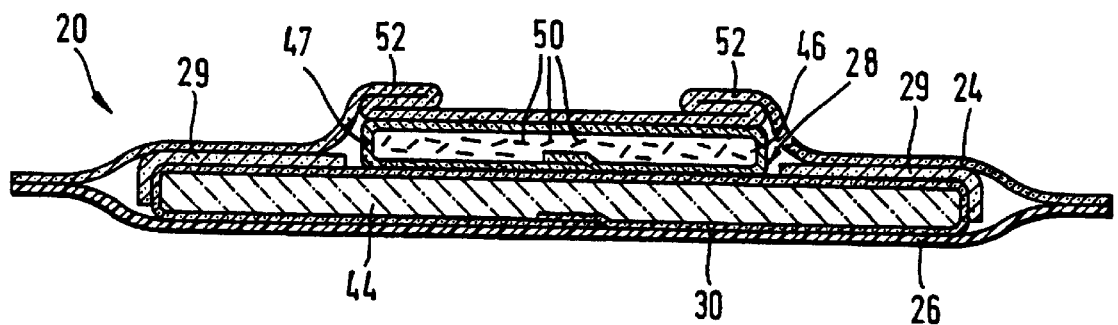
FIG. 6 is a cross-sectional view similar to that of FIG. 2 of a further embodiment of a sanitary napkin according to the present invention.

In another alternative embodiment illustrated in FIG. 6 a sanitary napkin 20 similar to that illustrated in FIGS. 1 and 2 further comprises an acquisition layer or secondary topsheet 29 positioned between the topsheet 24 and the absorbent core 28. Preferably the acquisition layer 29 does not completely overlie the absorbent core 28; in the embodiment illustrated in FIG. 6 the acquisition layer 29 does not cover the expanding layer 46 that is therefore capable of receiving the body fluids directly through the topsheet 24. As illustrated in FIG. 6 the acquisition layer 29 has a discontinuous surface comprising a window which is slightly longer and wider than the expanding layer 46; therefore the acquisition layer 29 is actually comprised between the topsheet 24 and the substantially non expanding absorbent element 44 of the absorbent core 28. Alternate configurations may also be possible, e.g. the acquisition layer 29 may comprise two narrow strips longitudinally oriented and positioned over the absorbent element 44 of the absorbent core 28 at both sides of the expanding layer 46. Alternatively, the acquisition layer 29 can be comprised between the absorbent core 28 and the backsheet 26; further, the acquisition layer 29 can be comprised between the expanding layer 46 and the absorbent element 44 in an embodiment similar to that illustrated in FIG. 2.

The acquisition layer 29 may serve several functions including improving wicking of body fluids that directly reach the acquisition layer 29 over and into the absorbent core 28. In the embodiment illustrated in FIG. 6 the acquisition layer 29 may also receive fluid that may escape laterally from the expanding layer 46 and direct it into the absorbent element 44 of the absorbent core 28. By improving wicking of body fluids, the acquisition layer 29 provides a more even distribution of the body fluids throughout the absorbent core 28.

The acquisition layer 29 preferably comprises materials that are capable of acquiring liquid very fast, and subsequently release it to contiguous layers with substantially no retention capacity.

The acquisition layer 29 may be comprised of several different materials including nonwoven or woven webs of synthetic fibres including polyester, polypropylene, or polyethylene; natural fibres including cotton or cellulose; blends of such fibres; or any equivalent materials or combinations of materials. Examples of sanitary napkins having an acquisition layer and a topsheet are more fully described in U.S. Pat. No. 4,950,264 issued to Osborn and U.S. patent application Ser. No. 071810,774, "Absorbent Article Having Fused Layers", filed Dec. 17, 1991 in the names of Cree, et al.

The topsheet 24, the acquisition layer 29 and the absorbent core 28 may also be associated in any suitable manner, in order to insure proper fluid transfer between them. In a further alternative embodiment that is not illustrated the acquisition layer 29 may be interposed between the topsheet 24 and the underlying absorbent core 28 comprising the expanding layer 46; the acquisition layer 29 must be left free to follow the expansion of the expanding layer 46 upon absorption of liquid, without restraining its swelling.

In the embodiment illustrated in FIG. 6 the expanding layer 46 completely corresponds to that described according to FIGS. 1 and 2, comprising randomly arranged smaller expanding elements 50.

Figure 7:
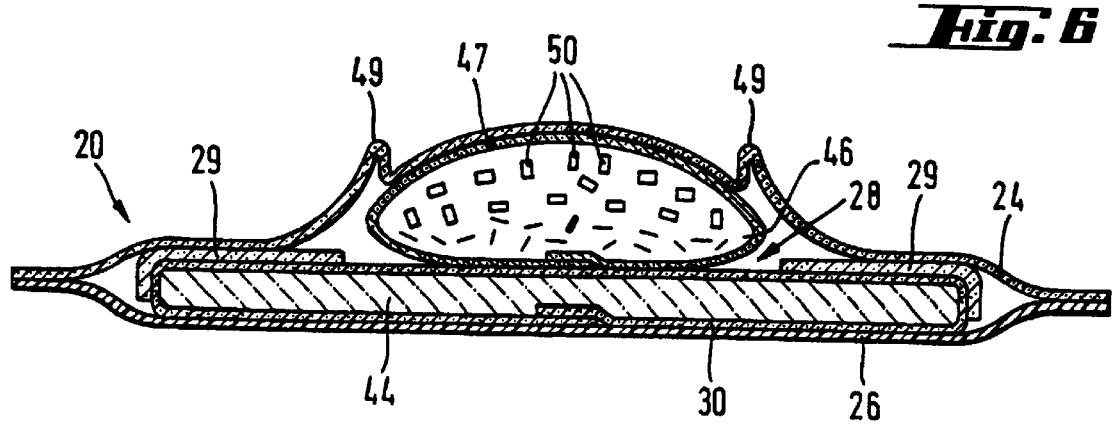
FIG. 7 is a cross-sectional view showing the sanitary napkin of FIG. 6 expanded in a tridimensional structure after activation during wear.

As illustrated in FIG. 6, the pleats or folds 52 are positioned at both sides of the longitudinal centreline O—O and substantially parallel to it, but in each pleat or fold 52 the topsheet 24 is folded twice on itself toward the longitudinal centreline O—O of the sanitary napkin 20. During the swelling of the expanding layer 46 upon fluid absorption the straightening out of the pleats or folds 52 forms a sort of longitudinally oriented side cuffs 47 that provide a better seal against side leakage, as illustrated in FIG. 7; the side cuffs 47 may still be present when the swelling of the expanding layer 46 is completed if the overall width of the topsheet 24 is slightly higher than that which would be necessary to follow the complete swelling of the expanding layer 46.

Although the disposable absorbent article of the present invention has been described with reference to a sanitary napkin, it can be used beneficially in the context of other disposable absorbent articles such as panty liners, incontinence articles and diapers. The disposable absorbent article may thus also have all those features and parts which are typical for products in the context of their intended use.

What is claimed is:

1. A disposable absorbent article for wearing adjacent a body discharge area, said article having a longitudinal centerline and a lateral centerline orthogonal to said longitudinal centerline and defining longitudinal and lateral directions respectively, said article further having a Z-direction which is orthogonal to both said longitudinal and said lateral directions, said article further comprising a liquid pervious topsheet, a backsheet joined to said topsheet, and an absorbent core intermediate said topsheet and said backsheet, said absorbent core having a body faceable surface and further comprising an expandable layer, said expandable layer having a body facing surface and a garment faceable surface and further comprising a number of smaller expandable elements activatable by body fluids which are decoupled from one another and randomly distributed within said expandable layer, wherein each said smaller expandable element is capable of expandable substantially in only one direction upon activation by body fluids and at least two different smaller expandable elements are capable of expanding in substantially two non-parallel directions, respectively, and wherein said smaller expandable elements of said expandable layer are made of compressed regenerated cellulose sponge having a dry density of 0.1 to 1 g/cc.

2. A disposable absorbent article according to claim 1, wherein said smaller expandable elements constitute from 10% to 100% of the total dry weight of said expandable layer.

3. A disposable absorbent article according to claim 1, wherein said expandable layer further comprises absorbent fibres.

4. A disposable absorbent article according to claim 1, wherein said smaller expandable elements have a dry volume comprised between 0.1 mm$^3$ and 150 mm$^3$.

5. A disposable absorbent article according to claim 1, wherein said expandable layer is capable of expandable said article into a tridimensional structure while being worn by a user upon activation by body fluids by expanding substantially in said Z-direction.

6. A disposable absorbent article according to claim 5 wherein when said absorbent article is placed in contact with a user's body, said expandable layer is capable of expandable outward to conform more closely to the body faceable surface of said absorbent article to the shape of the portion of the user's body with which said body faceable surface of the absorbent article is in contact.

7. A disposable absorbent article according to claim 5 wherein said liquid pervious topsheet is capable of expandable as the absorbent article expands into a tridimensional structure upon activation by body fluids.

8. A disposable absorbent article according to claim 1, wherein said expandable layer forms at least part of said body faceable surface of said absorbent core.

9. A disposable absorbent article according to claim 1, wherein said absorbent article is a sanitary napkin or a pantiliner.

* * * * *